United States Patent [19]
Gingold

[11] Patent Number: 5,197,648
[45] Date of Patent: Mar. 30, 1993

[54] SURGICAL STAPLING APPARATUS

[76] Inventor: Bruce S. Gingold, 36 Seventh Ave., New York, N.Y. 10011

[21] Appl. No.: 803,671

[22] Filed: Dec. 3, 1991

Related U.S. Application Data

[63] Continuation of Ser. No. 277,656, Nov. 29, 1988, abandoned.

[51] Int. Cl.$^5$ .............................................. A61B 17/00
[52] U.S. Cl. ..................................... 227/179; 227/19; 227/180; 227/175
[58] Field of Search .................. 227/19, 179, 175, 178, 227/180; 403/204, DIG. 4

[56] References Cited

U.S. PATENT DOCUMENTS

| | | | |
|---|---|---|---|
| 1,353,299 | 9/1920 | Wilson | 403/DIG. 4 |
| 1,904,061 | 4/1933 | Larson | 403/DIG. 4 |
| 3,193,165 | 7/1965 | Akhalaya et al. | 227/DIG. 1 |
| 4,198,982 | 4/1980 | Fortner et al. | 227/19 |
| 4,351,466 | 9/1982 | Noiles | 227/DIG. 1 |
| 4,476,863 | 10/1984 | Kanshin et al. | 227/19 X |
| 4,505,272 | 3/1985 | Utyamyshev et al. | 227/179 |
| 4,573,468 | 3/1986 | Conta et al. | 227/DIG. 1 |
| 4,592,354 | 6/1986 | Rothfuss | 227/DIG. 1 |
| 4,665,917 | 5/1987 | Clanton et al. | 227/DIG. 1 |
| 4,752,024 | 6/1988 | Coreen et al. | 227/DIG. 1 |
| 4,817,847 | 4/1989 | Redienbacher et al. | 227/19 |
| 4,873,977 | 10/1989 | Avant et al. | 227/19 X |

FOREIGN PATENT DOCUMENTS

| | | | |
|---|---|---|---|
| 3300768 | 4/1985 | Fed. Rep. of Germany | 227/179 |
| 8706448 | 11/1987 | PCT Int'l Appl. | 227/19 |

*Primary Examiner*—Paul A. Bell
*Attorney, Agent, or Firm*—Klauber & Jackson

[57] ABSTRACT

An improved circular anastomosis surgical stapling instrument for joining hollow tubular organs, has a body having a staple-carrying assembly at its distal end, a centered longitudinally extensible and retractable main shaft centered in the body, and an anvil opposed to the staple-carrying assembly, and is characterized by a separate shaft segment frictionably connectible with the end of the main shaft, the shaft segment having a free end and an end carrying the anvil. The main shaft has a hollow free end and the free end of the shaft segment is releasably receivable in the hollow end of the main shaft. In a preferred form the end of the main shaft is provided with a plurality of several radially-extending arms positioned to overlie the main shaft but having spring hinges biasing them radially outwardly away from the main shaft. The instrument further includes a second shaft segment releasably receivable in the hollow of the main shaft which second shaft segment has a concial pointed unit at its distal end.

4 Claims, 1 Drawing Sheet

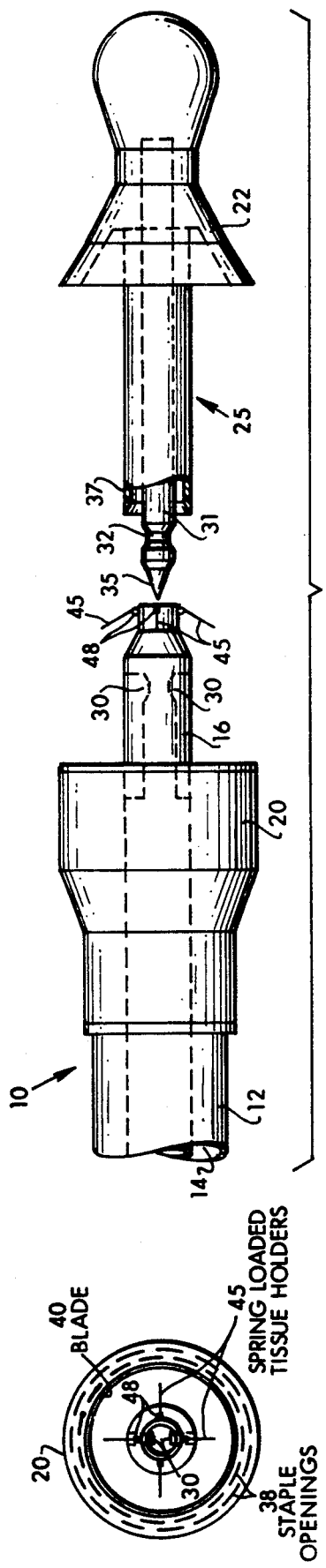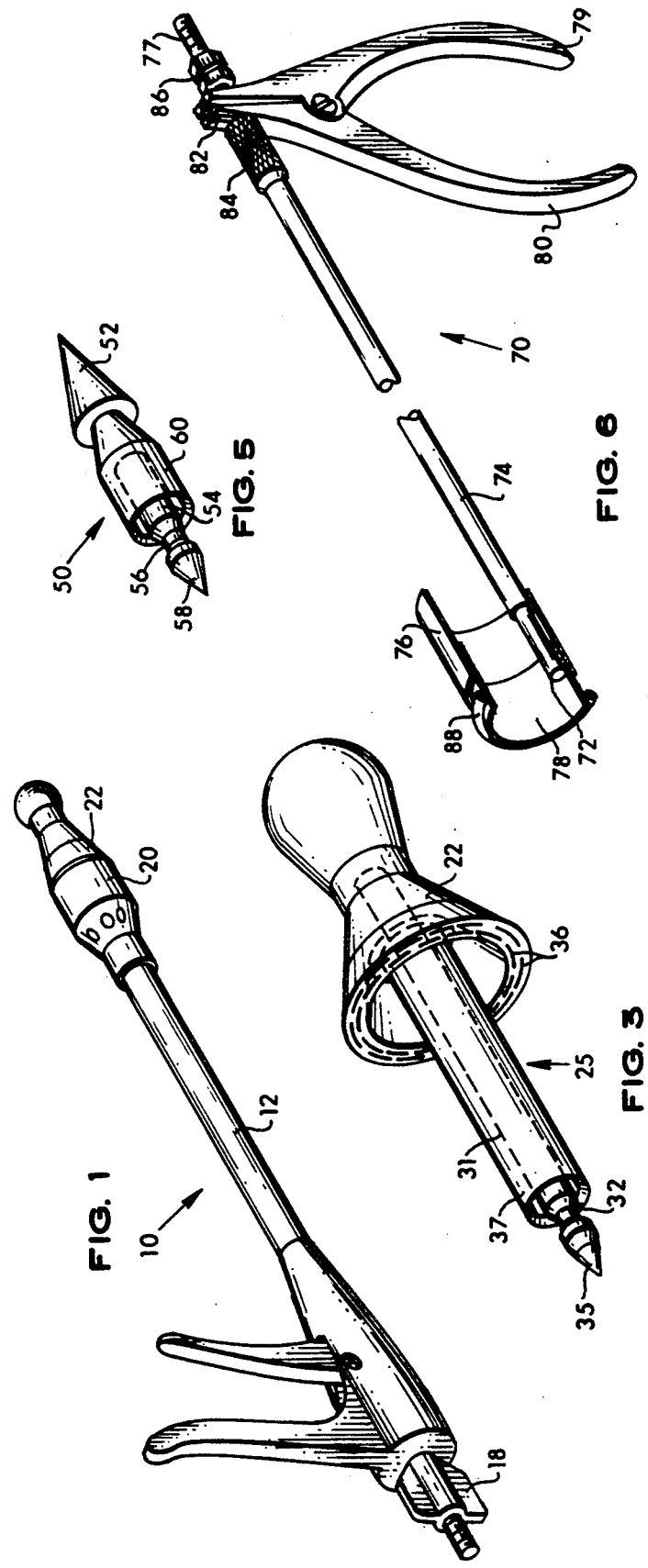

SURGICAL STAPLING APPARATUS

This application is a continuation of application Ser. No. 277,656, filed Nov. 29, 1988 now abandoned.

FIELD OF THE INVENTION

This invention relates to a surgical stapling apparatus and is more particularly concerned with an improved circular anastomosis surgical stapler.

BACKGROUND OF THE INVENTION

There are several known types of surgical staplers in which the stapling function takes place at a location which is relatively remote from the location at which the stapler is held and actuated by the operator. Examples of such staplers are the circular anastomosis surgical staplers shown illustratively in Akhalaya et al, U.S. Pat. No. 3,193,165 and Noiles U.S. Pat. No. 4,351,466. Typically, instruments of the types exemplified by these references, include a main body which is provided with a staple-holding assembly at its distal end and a longitudinal connecting shaft which is axially movable within the body and extends outwardly from the distal end of the body. The anvil assembly is fixed or threaded onto the free end of the shaft so that, when the shaft is caused to reciprocate with respect to the body, the anvil assembly can be caused to move toward and away from the staple-holding assembly. When such an instrument is used, tissue to be stapled is fastened about the staple-holding assembly and about the anvil assembly and clamped between them. The clamped tissue is then stapled by driving a plurality of staples from the staple-holding assembly so that the ends of the staples pass through the tissue and are clinched by contact with the anvil assembly. The forces required to operate the instrument to eject the staples are applied by the operator of the instrument to one or more actuator elements located at or near the proximal end of the body of the instrument. Means are also provided for causing the shaft to advance and retract. These means are generally at the proximal end of the body of the instrument. Thus, the distal and proximal portions of the instrument are joined by the longitudinal connecting shaft structure along which the actuating forces and motions are transmitted to the distal operating elements. This type of construction, including relatively widely-spaced distal and proximal portions, is conventionally used.

In a typical procedure, e.g. in colon surgery, the sections of the colon to be joined are, respectively, secured manually about the staple-holding assembly and the adjacent shaft portion and about the anvil of the instrument and the adjacent shaft portion. The head and anvil are then drawn together by causing the longitudinal connecting shaft to the end of which the anvil assembly is rigidly mounted to retract in the instrument body, so that the anvil assembly approaches the staple-holding assembly carried by the instrument body, and thereupon the stapling operation ensues.

A serious problem with the procedure just described is that, when using surgical stapling devices of the prior art, the surgeon must work "blind" to some extent since the staple-holding assembly and the anvil assembly are each rigidly connected to the instrument at a limited distance from each other and he must apply the tissue in a limited space and, at times, he cannot fully view all parts of the tissue to be stapled. Vision is limited by the rigid relationship between the staple-carrying assembly and the anvil assembly so that the gap or distance between the two is often unduly confining. In addition, because the anvil blocks the surgeon's view, as frequently happens, if the purse-string sutures fixing the bowel around the instrument are loose or incomplete, after the instrument is fired and withdrawn, the anastomosis has to be redone. Even worse, occasionally, this is not recognized and a leak can occur, resulting in pelvic infection or worse.

Currently, surgical stapling instruments are constructed so that they can be economically discarded after use in a single surgical procedure, i.e., so-called disposable instruments. Typically, a disposable instrument is sold in sterile condition in packaging designed to keep the instrument sterile until used. After the instrument has been used in a surgical procedure, it is discarded. In this way, all difficulty and expense associated with cleaning, sterilizing, and reloading the instrument are entirely avoided.

For an instrument to be economically disposable after use in only one surgical procedure, however, the cost of the instrument must be relatively low. This generally dictates that as much as possible of the instrument be made of inexpensive materials such as plastics, and that the instrument have the simplest and lightest possible construction. These criteria for an economically disposable instrument require a non-complicated construction for the instrument.

OBJECTS OF THE INVENTION

In view of the foregoing, it is an object of this invention to provide an improved surgical stapler of the type having distal stapling elements and proximal actuating elements.

It is another object of this invention to provide an improved surgical stapler of the character described which is economically disposable.

It is a further object of this invention to provide an improved circular anastomosis surgical stapler.

It is a still further object of this invention to provide an improved circular anastomosis surgical stapler which will give the surgeon increased freedom of action, as well as improved visibility, to ensure proper stapling and thus improved results and safety for patents.

SUMMARY OF THE INVENTION

These and other objects of the invention are accomplished in accordance with the principles of the invention by providing a surgical stapler which includes a longitudinal shaft assembly which is movable axially within a hollow stapler body which has a staple-carrying assembly at its distal end, the invention being characterized by a separable shaft segment removably connected to the main body of the portion shaft so that the shaft portion which projects from the stapler body is in two connectible but separable parts. i.e. the distal end of the shaft is made separable by the provision of the removable end segment which carries the anvil assembly. In a preferred form of the invention, the free end of the shaft which remains after the end segment is removed, is provided with movable tissue-restraining members to prevent tissue from slipping off the shaft end, and the removable end segment, which releasably interconnects with the free end of the shaft, if formed with a shroud or hood which depresses the restraining members when the end segment and the main body of the shaft are releasably joined. Also contemplated are separable puncturing means releasably connectable with the free end of the shaft prior to using the anvil-carrying segment, and means for rapidly binding tissue to the free end of the shaft adjacent the staple-carrying assembly of the stapler body and to the shaft segment carrying the anvil.

BRIEF DESCRIPTION OF THE DRAWINGS

These and other features and objects of the invention will be apparent from the drawings wherein, FIG. 1 is a perspective view of a typical standard circular anastomosis surgical stapler;

FIG. 2 is an enlarged view of the distal end of a stapler of the character indicated which is constructed to embody features of the present invention;

FIG. 3 is a perspective view of the separable anvil-carrying end segment of the structural assembly shown in FIG. 2;

FIG. 4 is an end view of stapler body assembly shown in FIG. 3;

FIG. 5 is a perspective view of a tissue-puncturing element optionally usable with the stapler body assembly; and FIG. 6 is a perspective view of a device for attaching tissue about the shaft projecting from the stapler body and about the separable shaft segment.

DETAILED DESCRIPTION OF THE PREFERRED EMBODIMENTS

Referring now to the drawings, and particularly to FIG. 1, there is shown a typical circular anastomosis surgical stapler of the type used for end-to-end anastomosis and thus known as an EEA Stapler and indicated generally by the reference number 10. A stapler of this nature is shown, for example in Noiles U.S. Pat. No. 4,351,466 in Conta U.S. Pat. No. 4,573,468 and in Clanton U.S. Pat. No. 4,665,917, the disclosures of which are incorporated herein by reference. Stapler 10 has an elongated hollow tubular body or housing 12 which has an axial bore 14 through which extends a shaft 16 which can be reciprocated i.e. extended and retracted, in the body 12 by means of a control nut 18 at the proximal end of the instrument 10. The body 12 has at its distal end a staple-carrying assembly 20. In a conventional circular anastomosis surgical stapler, the shaft 16 carries at its distal end an anvil assembly 22 threadedly or fixedly engaged with it, i.e. the shaft 16 is continuous as it extends through the staple-carrying assembly 20 to the anvil assembly 22, which anvil assembly is rigidly connected to the entire shaft when it has been been screwed into place.

In accordance with the invention, however, as seen in FIG. 2, the portion of the shaft which is visible when it has been extended out of the housing 12 to its greatest length, is not a continuous shaft but, rather, has a frictionally-separable end portion or segment 25. The anvil 22 is fixedly secured to the distal end of the shaft segment 25. The frictionally-separable segment 25 can be frictionally engaged with the end portion of shaft 16 in any convenient manner but, in the embodiment illustrated and in a preferred form of the invention, the end portion of shaft 16 is hollow and formed with interior flexible detents 30. At the same time, shaft segment 25 is formed with a shaft portion 31 dimensioned to be received in the hollow of shaft 16 but of greater diameter than the space between detents 30. Shaft portion is formed with an annular recess 32. The detents 30 are positioned to receive the proximal end portion 31 of the shaft segment 25 between them and to engage in the recess 32 which is formed in proximal end portion 31 carried by the segment 25. Conveniently, the shaft end portion 31 may have a point 35 at its proximal end in order to facilitate guiding the portion 31 into the hollow distal end of the main body of shaft 16 when the segment 25 and the main body of shaft 16 are to be releasably interconnected.

As seen in FIG. 3, the anvil of the releasable segment 25 is of conventional construction and has surfaces 36 for suitably crimping or clinching the ends of the staples when they are ejected from the staple-carrying end of the instrument and after they pass through the tissue to be stapled. As seen in FIG. 4, the staple-carrying distal end of body 12 contains a plurality of surgical staples (not shown) pointing towards the distal end of the instrument and arranged in two concentric annular rows. Shown in FIG. 4 are the openings 38 through which the staples are ejected. Conventionally, the staple-carrying assembly 20 also contains a circular knife 40 which is on the radially-inner side of the annular staple array. The staples and blade are of known construction and form no part of the present invention. In accordance with the invention, however, as previously mentioned, the distal end of the main shaft 16 is hollow and is interiorly formed with detents 30, the purpose of which has been indicated above. In addition, in accordance with a preferred form of the invention, the distal end of the main body of the shaft 16 is formed with spring-loaded tissue holders or restrainers 45. The restrainers 45 are at least two in number but most suitably may be greater in number, such as the four restrainers illustrated in the drawings. They are connected to the shaft 16 by means of spring hinges 48 which permit the restrainers to lie flat against the shaft but normally urge the ends of the restrainers away from the shaft into an acute-angled position, as illustrated. Referring again to the right-hand portion of FIG. 2, which shows the releasable segment 25 of shaft 16, it will be seen that the shaft portion 31 previously mentioned is surrounded by an outer shroud member 37 which has in internal surface which is spaced from the shaft portion 31 by a distance at least as great as the length of the tissue restrainers 45. As will be apparent from FIG. 2, when the segment 25 is interlocked with the main body portion of shaft 16, by inserting the shaft portion 31 into the hollow end of shaft 16 until detents 30 are received in recess 32, the shroud 54 will strike and cause the tissue restrainers 45 to lie closer to the surface of the distal end of shaft 16 and will enclose them as the detents 30 enter recess 32 and the separable segment 25 is locked into place as a separable extension of shaft 16.

In using the instrument of the invention, e.g. for an end-to-end anastomosis during rectal surgery, the sections to be joined by stapling, e.g., the ends of proximal bowel and the rectum, must be tied around the shafts 16 and 25 with purse-string sutures. This may be a exacting process, especially for the rectal end if deep in the pelvis. The instrument is inserted into the bowel and advanced until the anvil protrudes through the rectal lumen. The stapler is then opened fully by advancing the shaft 16. The shaft segment 25 with the anvil 22 attached to it is then separated from the shaft 16 by pulling the shaft segment 25 to release recess 32 from detents 30. As this occurs, tissue restrainers 45 are urged outwardly by spring hinges 48 so that the sutured rectum, or other tissue to be stapled, will be held in place on the exposed end of shaft 16, and accidental dislodgement is effectively prevented. Such dislodgement frequently occurs when using currently constructed staplers. The sutured proximal bowel or other opposed tissue to be stapled is then advanced over the now-released and freely movable anvil 22. The distal purse string is then secured around the end of shaft 16 between the end of body 14 and restrainers 45 and the proximal purse string is similarly secured around shaft segment 25. Since the staplecarrying assembly 20 and the anvil assembly 22 are completely separate from each other, the surgeon has complete freedom of movement and visibility and is not hampered or constrained by limitations of the stapling instrument as he would have been when using instruments of the prior art. After the securing of the tissue has been completed, the shaft segment 25 is again interconnected with the main shaft 16 by inserting shaft end portion 31 into the hollow end of shaft 16 until detents 30 interlock in recess 32. While this is occurring, shroud 37 forces restrainers 45 downwardly and overlies and conceals them, leaving the tissue secured about the shaft 16 free to be stapled. The anvil 22, with the opposed tissue to be stapled secured about shaft segment 25, is then drawn toward staple-carrying assembly 20 the desired amount and the staples fired, the circular knife 40 simultaneously cutting two rings of tissue radially inside the staple line, thus creating the desired end-to-end anastomosis. The anvil 22 is then removed by disengaging end shaft portion 31 from detents 30 as described above. The anvil and its attached shaft segment 25 are then removed from the lumen by making a suturable opening in the wall of the bowel and removing the anvil assembly from the bowel lumen in the same manner as threadedly-engaged anvils are conventionally removed. The shaft 16 and the staple-carrying assembly 20 are removed from the opposed lumen in conventional manner simply by carefully withdrawing the instrument body.

While end-to-end anastomosis has been described, for which the instrument is particularly adapted, it will be apparent that the improved instrument of the invention can be used for other anastomosis procedures such as end-to-side, side-to-side and side-to-end anastomoses.

An important feature of the invention is that, by reason of the provisions of a two-part separable shaft, it permits optional use of shaft attachments or extensions other than the shaft segment 25 with its attached anvil 22.

Thus, it sometimes occurs that the purse-string sutures are too tightly originally formed or the rectal end intentionally oversewn completely, either during this operation or during previous surgery, so that the instrument with interconnected anvil cannot be conveniently passed through the lumen unless the opening is enlarged.

For this purpose, in accordance with the invention, there is provided a temporarily-attachable device. Thus, referring to FIG. 5, there is shown a puncturing and enlarging unit 50. Unit 50 has a sharply-pointed conical head 52 a shaft portion 54, corresponding to shaft end portion 31. Like shaft end portion 31, shaft portion 54 is formed with a recess 56 for reception of detents 30, and conveniently may have a pointed end 58 to guide it into the hollow end of shaft 16. It is also provided with a shroud 60.

When it is desired to use unit 50, the anvil assembly with its shaft end 31 is disengaged from shaft 16, simply by pulling it to release detents 30 from recess 32, and it is replaced at the end of shaft 16 by inserting shaft portion 54 into the end of the hollow end of shaft 16 until the detents 30 engage in recess 56. The instrument 10, with the unit 50 attached, is then used to pierce and open the closed end of the lumen so that the anvil and the staple-carrying assembly may readily pass through it. Thereupon, the instrument is withdrawn, the unit 50 disengaged and replaced by shaft segment 25 and its attached anvil 22, and the procedure of anastomosis can proceed as described above.

In accordance with another aspect of the invention, means are provided for cooperating with the improved anastomosis instrument above described to facilitate securing tissue on the instrument for stapling in a rapid, convenient manner, thus avoiding the difficult task of saturing the edge of the rectal end around shaft 16.

Thus, referring to FIG. 6, there is shown a perspective of a tissue-securing device 70 which comprises a rod 72 telescoped and slidable within a tube 74. The shells 76 and 78 are illustrated in FIG. 6 as cylindrical fragments in order to show details of construction. At its distal end tube 74 is secured to cylindrical shell 76. Rod 72 is secured to cylindrical shell 78 which is telescopingly slidable within shell 76. The relationship of telescoping shells 76 and 78 to each other is such that when rod 72 is extended from tube 74, the distal edge of shell 78 will extend beyond the distal edge of shell 76, but rod 72 can be retracted so that the distal edge of shell 78 will coincide with the distal edge of shell 76.

The mechanism for telescopingly moving shells 76 and 78 is shown at the right in FIG. 6. The free end of rod 72 is threaded, as seen at 77. An arm 79 is pivotally connected to an arm 80. Arm 78 is threadedly-engaged with threaded end 76. Arm 80 is bifurcated at its end, as seen at 82, and is received in a slot (not shown) in rod 72 adjacent the free end 84 of tube 74. Threaded end 76 also carries a nut 86. The device 70 is employed to discharge an elastic band of circular cross-section 88. Thus, the band 88 is placed about the shell 78. When shell 78 is retracted within shell 76 by squeezing arms 78 and 80, band 88 is forced off shell 78 and discharged. It is a feature of the invention that the device 70 can be used to secure tissue to be stapled about shaft 16 and about releasable segment 25. For this purpose, shells 76 and 78 are given an internal diameter somewhat smaller then the external diameter of the staple-carrying assembly 20 and the external diameter of the anvil 22 but sufficiently greater than the external diameter of rod 16 and segment 25 such that the shells will easily receive the ends of rod 16 and of segment 25 as well as tissue overlying them. Thus, the device 70 is used after tissue to be stapled has been placed about the distal end of body 12 and about the free end of shaft 16, as well as about shaft segment 25, but before the anvil assembly has been united with the end of shaft 16. For this purpose shell 78 is extended, the round elastic band 88 is placed about it, and shell 78 is positioned to enclose the free end of shaft 16 and the tissue overlying it. Then handles 79 and 80 are squeezed, and the band 88 is discharged as shell 78 is retracted within shell 76. The band 88 thereupon secures the tissue about the shaft. Shell 78 is again extended by separating handles 79 and 80, a band 88 is placed about shell 78, shell 78 is positioned to surround the tissue overlying shaft segment 25, and the procedure above described is repeated to discharge the band 88 and secure the tissue about shaft segment 25. The above-described procedure easily and safely fixes the tissue ends, e.g. the bowel ends, permitting an improved anastomosis. In particular, this procedure prevents the bowel distal end which is to be stapled from slipping off the end of the instrument. When the stapling device 10, with its circular knife 40, is actuated, the portion of the tissue within the staple line cut out by the knife will include the bands 88 so that they will be removed from the lumen when the device and the separable anvil assembly 22 with attached segment 25 are removed.

It will be obvious that various changes and modifications may be made without departing from the invention as defined in the appended claims and it is intended, therefore, that all matter contained in the forgoing description and in the drawing shall be interpreted as illustrative only and not as limitative of the invention.

I claim:

1. In combination circular anastomosis surgical stapling instrument for joining hollow tubular organs, said instrument including a body having a staple-holding and ejecting assembly at its distal end, a centered longitudinally-extensible main shaft and an anvil opposed to said staple-holding and ejecting assembly, the improvement which comprises a separate shaft segment frictionally connectible with the end of said main shaft, said shaft segment having a free end and an end carrying said anvil, the end of said main shaft being provided with a plurality of radially-extending arms positioned to overlie said main shaft but said arms having spring hinges biasing them radially outwardly away from said main shaft.

2. A stapling instrument as defined in claim 1, wherein said main shaft has a hollow free end portion carrying flexible detents, the free end of said shaft segment being releasably receivable by means of said flexible detents in said hollow end portion.

3. A stapling instrument as defined in claim 1, further including in combination a second shaft segment releasably receivable by means of flexible detents in said hollow end portion, said second shaft segment having a conical pointed unit at its distal end.

4. In combination with a circular anastomosis surgical stapling instrument for joining hollow tubular organs, said instrument including a body having a staple-holding and ejecting assembly at its distal end, a centered longitudinally-extensible main shaft and an anvil opposed to said staple-holding and ejecting assembly, and a separate shaft segment frictionally connectible with the end of said main shaft, said shaft segment having a free end and an end carrying said anvil; a band-attaching device comprising two telescopically related shells, and means for extending and retracting one of said shells relatively to the other, said shells being dimensioned to enclose the end of said shaft and of said shaft segment and having an internal diameter somewhat smaller than the outside diameter of said anvil.

* * * * *